(12) United States Patent
Wan

(10) Patent No.: US 10,151,711 B2
(45) Date of Patent: Dec. 11, 2018

(54) METHOD AND APPARATUS FOR GENERATING X-RAY INSPECTION IMAGE OF ELECTRONIC CIRCUIT BOARD

(71) Applicant: SHENZHEN KANA TECHNOLOGY CO., LTD., Shenzhen (CN)

(72) Inventor: Wenxue Wan, Shenzhen (CN)

(73) Assignee: SHENZHEN KANA TECHNOLOGY CO., LTD., Shenzhen (CN)

( * ) Notice: Subject to any disclaimer, the term of this patent is extended or adjusted under 35 U.S.C. 154(b) by 46 days.

(21) Appl. No.: 15/611,834

(22) Filed: Jun. 2, 2017

(65) Prior Publication Data

US 2017/0269007 A1    Sep. 21, 2017

Related U.S. Application Data

(63) Continuation of application No. PCT/CN2014/095655, filed on Dec. 30, 2014.

(30) Foreign Application Priority Data

Dec. 5, 2014 (CN) .......................... 2014 1 0736262

(51) Int. Cl.
*G01N 23/00* (2006.01)
*G01N 23/04* (2018.01)
(Continued)

(52) U.S. Cl.
CPC ........... *G01N 23/04* (2013.01); *G01R 31/309* (2013.01); *H05G 1/02* (2013.01); *H05G 1/10* (2013.01); *H05G 1/265* (2013.01); *H05G 1/30* (2013.01)

(58) Field of Classification Search
CPC ...................................................... G01N 23/04
See application file for complete search history.

(56) References Cited

U.S. PATENT DOCUMENTS

| 6,237,218 B1 | 5/2001 | Ogawa et al. |
| 2001/0028732 A1 | 10/2001 | Coulombe |

(Continued)

FOREIGN PATENT DOCUMENTS

| AT | 247309 T | 8/2003 |
| AU | 2821101 A | 7/2001 |

(Continued)

OTHER PUBLICATIONS

International Search Report dated Jun. 9, 2016 for Application No. PCT/CN2014/095655.

(Continued)

*Primary Examiner* — Dani Fox
(74) *Attorney, Agent, or Firm* — Na Xu; IPro, PLLC

(57) ABSTRACT

A method and an apparatus for generating x-ray inspection image of an electronic circuit board are disclosed. The method includes: respectively generating, according to data files of the electronic circuit board and parameters of an X-ray machine, analog images of both faces of the electronic circuit board; subjecting the electronic circuit board to X-ray imaging to generate a real image of the electronic circuit board, the real image comprising real image elements on both faces of the electronic circuit board; identifying, according to the analog images of both faces, from the real image an interference image element that needs to be filtered from the real image for generating a real image of a detected object; and filtering the interference image element from the real image to generate the real image of the detected object.

21 Claims, 8 Drawing Sheets

(51) Int. Cl.
*G01R 31/309* (2006.01)
*H05G 1/02* (2006.01)
*H05G 1/10* (2006.01)
*H05G 1/26* (2006.01)
*H05G 1/30* (2006.01)

(56) References Cited

U.S. PATENT DOCUMENTS

2005/0087886 A1  4/2005  Leinbach
2006/0274883 A1* 12/2006  Buck .................. G01N 23/04
                                              378/57
2014/0003578 A1  1/2014  Omote et al.

FOREIGN PATENT DOCUMENTS

| CA | 2296143 A1 | 7/2001 |
|---|---|---|
| CA | 2397382 A1 | 7/2001 |
| CN | 1401107 A | 3/2003 |
| CN | 1611929 A | 5/2005 |
| CN | 1869667 A | 11/2006 |
| CN | 103543167 A | 1/2014 |
| CN | 103543168 A | 1/2014 |
| DE | 60100594 T2 | 6/2004 |
| EP | 1254431 A1 | 11/2002 |
| IL | 150744 A | 9/2007 |
| JP | 2003520969 A | 7/2003 |
| JP | 3708133 B2 | 10/2005 |
| KR | 100744212 B | 7/2007 |
| PH | 1200100101 B1 | 9/2005 |
| SG | 121887 A1 | 5/2006 |
| TW | 200515248 A1 | 5/2005 |
| TW | 1240223 B | 9/2005 |
| WO | 9833366 A1 | 7/1998 |
| WO | 0154068 A2 | 7/2001 |

OTHER PUBLICATIONS

Fei Xian, The Application of X-ray Inspection in PCB Assembly, Special equipment for the electronics industry, Nov. 30, 2011, pp. 31-35, Issue No. 11, CN.

* cited by examiner

METHOD AND APPARATUS FOR GENERATING X-RAY INSPECTION IMAGE OF ELECTRONIC CIRCUIT BOARD

CROSS-REFERENCE TO RELATED APPLICATIONS

This application is a continuation of International Application No. PCT/CN2014/095655, with an international filing date of Dec. 30, 2014, which is based upon and claims priority to Chinese Patent Application No. 201410736262.4, filed on Dec. 5, 2014, the entire contents of all of which are incorporated herein by reference.

TECHNICAL FIELD

The present disclosure relates to the technical field of electronic circuit board inspection, and in particular, relates to a method and an apparatus for generating x-ray inspection image of an electronic circuit board.

BACKGROUND

At present, use of array components such as QFN, BGA, Flip chip, CSP and the like are more and more widely being used. To ensure the welding quality at invisible welding points of these components during the process of assembling electronic circuit boards, X-ray inspection devices are gradually becoming more and more indispensable inspection tools. This is mainly because the X-ray device is capable of penetrating through packages and directly checking the quality of the welding points.

In the current market, X-ray inspection system applied to BGA and CSP are mainly categorized into two dimensional systems and CT systems. All these devices support offline operation or online operation, and may be used in online inspection and sampling inspection. Whether to select an offline device or an online device depends on the specific application scenario.

All the X-ray inspection devices, regardless of whether two-dimensional systems or CT systems, operate based on the principle of projecting X rays to an image receiver for imaging. An X-ray emitter tube emits X rays which penetrates through a test sample (for example, an electronic circuit board), and a projection is generated on the image receiver according to different absorption quantities of the X rays due to different densities and atomic weights of sample materials, wherein a higher density of the substance indicates a dark shadow. The shadow formed close to the X-ray emitter tube is greater, and the shadow formed far away from the X-ray emitter tube smaller.

A two-dimensional X-ray system simultaneously displays two-dimensional images of all the components on both sides of an electronic circuit board. A three-dimensional CT X-ray system re-constructs image information using a series of two-dimensional images to generate an image of a tangent plane. This technology generates an image of a cross section of a test sample. Another three-dimensional CT X-ray inspection is called X-ray laminography, which reconstructs an image of a cross section by combining image data of a cross section and meanwhile canceling image information of other cross sections. The X-ray laminography system may operate in an online mode or an offline mode. However, during online operation, the speed is low because reconstructing data using a plurality of images takes time. To be specific, a plurality of two-dimensional images and compli- cated operations are required to reconstruct information, and this process takes several minutes.

SUMMARY

An embodiment of the present disclosure provides a method for generating x-ray inspection image of an electronic circuit board. The method includes:
respectively generating, according to data files of the electronic circuit board and parameters of an X-ray machine, analog images of both faces of the electronic circuit board;
subjecting the electronic circuit board to X-ray imaging to generate a real image of the electronic circuit board, the real image comprising real image elements on both faces of the electronic circuit board;
identifying, according to the analog images of both faces, from the real image an interference image element that needs to be filtered from the real image for generating a real image of a detected object; and
filtering the interference image element from the real image to generate the real image of the detected object.

Another embodiment of the present disclosure provides a method for generating x-ray inspection image of an electronic circuit board. The method includes:
subjecting the electronic circuit board to X-ray imaging to respectively generate a single-faced real image and a double-faced real image of the electronic circuit board;
identifying, according to the single-faced real image, from the double-faced real image an interference image element that needs to be filtered for generating a real image of a detected object; and
filtering the interference image element from the double-faced real image to generate the real image of the detected object.

Still another embodiment of the present disclosure provides an apparatus for generating x-ray inspection image of an electronic circuit board. The apparatus includes:
at least one processor; and
a memory communicably connected with the at least one processor for storing instructions executable by the at least one processor, wherein execution of the instructions by the at least one processor causes the at least one processor to:
respectively generate, according to data files of the electronic circuit board and parameters of an X-ray machine, analog images of both faces of the electronic circuit board;
subject the electronic circuit board to X-ray imaging to generate a real image of the electronic circuit board, the real image comprising real image elements on both faces of the electronic circuit board;
identify, according to the analog images of both faces, from the real image an interference image element in the real image that needs to be filtered for generating a real image of the detected object; and
filter the interference image element from the real image to generate the real image of the detected object.

Still another embodiment of the present disclosure provides an apparatus for generating x-ray inspection image of an electronic circuit board. The apparatus includes:
at least one processor; and
a memory communicably connected with the at least one processor for storing instructions executable by the at least one processor, wherein execution of the instructions by the at least one processor causes the at least one processor to:
subject an electronic circuit board to X-ray imaging to respectively generate a single-faced real image and a double-faced real image of the electronic circuit board;

identify, according to the single-faced real image, from the double-faced real image an interference image element that needs to be filtered for generating a real image of a detected object; and filter the interference image element from the double-faced real image to generate the real image of the detected object.

Still another embodiment of the present disclosure provides a non-transitory computer-readable storage medium storing executable instructions, wherein when executed by an apparatus, causes the apparatus to:

respectively generate, according to data files of a electronic circuit board and parameters of an X-ray machine, analog images of both faces of the electronic circuit board;

subject the electronic circuit board to X-ray imaging to generate a real image of the electronic circuit board, the real image comprising real image elements on both faces of the electronic circuit board;

identify, according to the analog images of both faces, from the real image an interference image element in the real image that needs to be filtered for generating a real image of the detected object; and filter the interference image element from the real image to generate the real image of the detected object.

Still another embodiment of the present disclosure provides a non-transitory computer-readable storage medium storing executable instructions, wherein when executed by an apparatus, causes the apparatus to:

subject an electronic circuit board to X-ray imaging to respectively generate a single-faced real image and a double-faced real image of the electronic circuit board;

identify, according to the single-faced real image, from the double-faced real image an interference image element that needs to be filtered for generating a real image of a detected object; and filter the interference image element from the double-faced real image to generate the real image of the detected object.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

DETAILED DESCRIPTION

For better understanding of the present disclosure, the present disclosure is described in detail with reference to attached drawings and specific embodiments.

It should be noted that, in the absence of conflict, embodiments of the present disclosure and features in the embodiments may be incorporated, which all fall within the protection scope of the present disclosure. In addition, although logic sequences are illustrated in the flowcharts, in some occasions, steps illustrated or described in the flowcharts may be performed in sequences different from those illustrated.

Unless the context clearly requires otherwise, throughout the specification and the claims, technical and scientific terms used herein denote the meaning as commonly understood by a person skilled in the art. Additionally, the terms used in the specification of the present disclosure are merely for description the embodiments of the present disclosure, but are not intended to limit the present disclosure.

Figure 1:
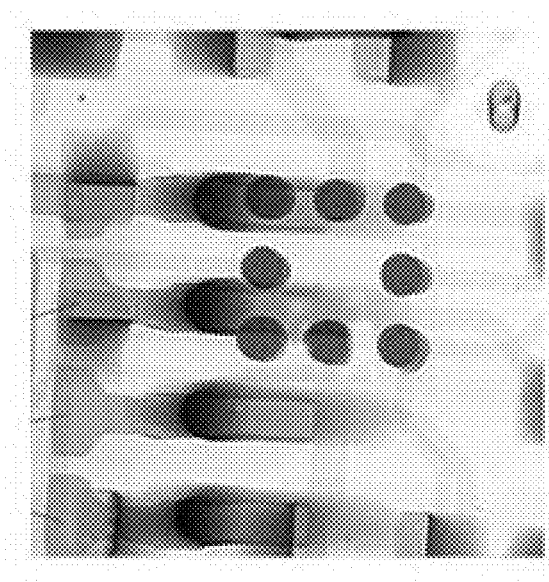
FIG. 1 is a schematic diagram of a real image of a double-faced electronic circuit board in the prior art.
Figure 2:
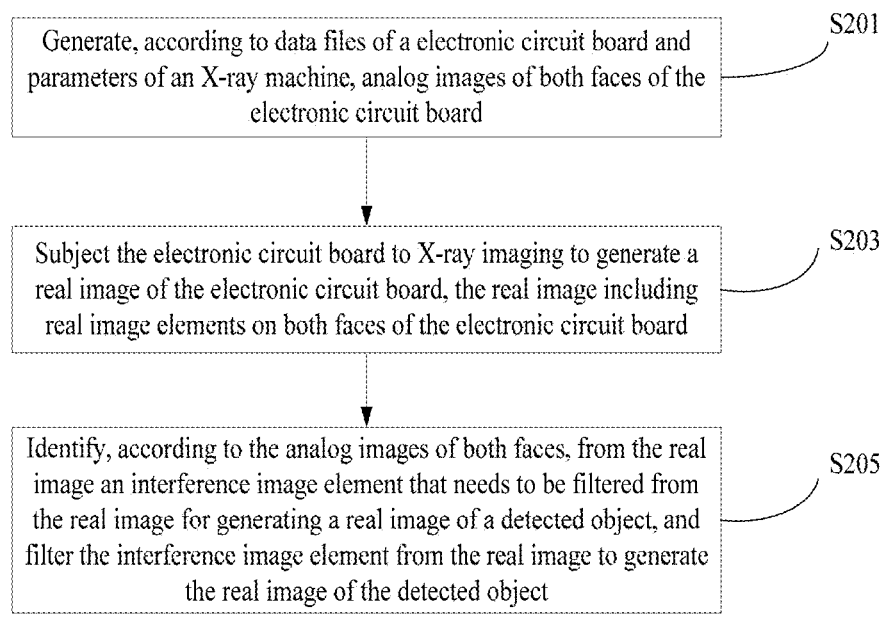
FIG. 2 is a schematic flowchart of a method for generating x-ray inspection image of an electronic circuit board according to an embodiment of the present disclosure.

FIG. 2 is a schematic flowchart of a method for generating x-ray inspection image of an electronic circuit board an electronic circuit board inspection method according to an embodiment of the present disclosure. As illustrated in FIG. 2, the method includes the following steps:

S201: Analog images of both faces of a electronic circuit board are respectively generated according to data files of the electronic circuit board and parameters of an X-ray machine.

In some embodiments of the present disclosure, the electronic circuit board may be a double-faced electronic circuit board, and the data files of the electronic circuit board may include CAD coordinate data of the electronic circuit board, a line design file of a printed circuit board and a component database. The CAD coordinate data may be exported from the design file of the electronic circuit board. The component parameters may be selected from a component standard library. If some special components are not defined in the standard library, a special component library may be defined by customization of users, and desired special components may be selected therefrom. The parameters of the X-ray machine may include X-ray tube voltage and/or target current. The parameters of the X-ray machine may be predefined or determined according to the line design file and the component parameters. For example, different X-ray tube voltages may be set for different X-ray machines according to empirical data, and the analog images of both faces that are substantially consistent with the real images of both faces may be obtained using computer software simulation.

In some embodiments of the present disclosure, the analog images of both faces of the electronic circuit board may be respectively generated according to the CAD coordinates data of the electronic circuit board, the line design file of the printed circuit board, the component parameters and the parameters of the X-ray machine, and with reference to imaging rules of different X-ray devices under different parameters of the X-ray machines.

S203: The electronic circuit board is subjected to X-ray imaging to generate a real image of the electronic circuit board, wherein the real image includes real image elements on both faces of the electronic circuit board.

In some embodiments of the present disclosure, the electronic circuit board may be directly subjected to X-ray imaging to generate a double-faced real image of the electronic circuit board covering elements on both front and back faces thereof. The image is the real image of the electronic circuit board, and includes all real elements on the front and back faces. If inspection is carried out by directly using this real image, due to mutual interference between the real elements on both faces, the device may fail to identify correct information of the detected object, and thus may fail to implement automatic inspection. As a result, on-line inspection may not be achieved. In some embodiments of the present disclosure, the real image is processed using the analog images generated in step S201. The detailed processing may be referenced to the description in step S205.

S205: An interference image element that needs to be filtered from the real image for generating a real image of a detected object is identified from the real image according to the analog images of both faces, and the interference image element is filtered from the real image to generate the real image of the detected object.

In some embodiments of the present disclosure, the process that an interference image element that needs to be filtered from the real image for generating a real image of a detected object is identified from the real image according to the analog images of both faces may include: identifying, according to analog images of both faces, from the real image real image elements corresponding to the analog images of both faces, and determining the interference image element that needs to be filtered from the real image for generating the real image of the detected object; wherein the analog images may be analog images of either face generated in step S201, and in the specific identification process computer software may be employed to compare the analog images with the real image to find the real image elements corresponding to the analog images from the real image. In addition, to generate the real image of the detected object, the interference image elements in the real image need to be filtered, wherein the interference image elements are a part or all of the real image elements corresponding to the analog images, and determination of an interference image element may be based on the analog images and the real image of the detected object to be generated.

In some embodiments of the present disclosure, the process that the interference image element is filtered from the real image to generate the real image of the detected object may include: filtering image features of the interference image element using image features of the real image to generate the real image of the detected object. The image features may include imaging gray scale and/or pixel.

In some embodiments of the present disclosure, the detected object may be a single-faced real image or may be a defined part of component.

If the detected object is a single-faced real image, the process that an interference image element that needs to be filtered from the real image for generating a real image of a detected object is identified from the real image according to the analog images of both faces in step S205 may include:

identifying, according to a front analog image, from the real image a front real image element corresponding to the front analog image, and determining an interference image element that needs to be filtered from the front real image for generating a back real image; or identifying, according to a back analog image, from the real image a back real image element corresponding to the back analog image, and determining an interference image element that needs to be filtered from the back real image for generating a front real image.

If the detected object is a defined part of component, the process that an interference image element that needs to be filtered from the real image for generating a real image of a detected object is identified from the real image according to the analog images of both faces in step S205 may include:

identifying, according to the analog image of each face, from the real image real image elements corresponding to the analog images of both faces, and determining the interference image element that needs to be filtered from the real image for generating the real image of the defined part of component.

In some embodiments of the present disclosure, a person skilled in the art may, in combination with the description in the embodiment, employ other methods to filter the real image elements corresponding to the analog images from the real image to obtain the real image of the detected object, which is not limited in the present disclosure. Any solution of generating the real image of the detected object via identification and calculation attained by a person skilled in the art according to the analog images in the embodiment of the present disclosure shall fall within the protection scope of the present disclosure.

In some embodiments of the present disclosure, the analog images and the real images may be two-dimensional images or may be images of other types. Any image filtering solution using the analog image technology according to the embodiment of the present disclosure shall fall within the protection scope of the present disclosure.

According to the embodiment of the present disclosure, by using generated analog images, an interference image element that needs to be filtered is identified from a real image, and a real image of a detected object is obtained by means of data calculation. In this way, on-line inspection of a double-faced electronic circuit board is implemented. With the method according to the present disclosure, online batchwise inspections do not need the CT technology. In addition, the method addresses the problem of X-ray image interference of the double-faced electronic circuit board, greatly simplifies the online inspection device of the electronic circuit board, and reduces the inspection device cost, and improves the inspection efficiency.

Figure 3:
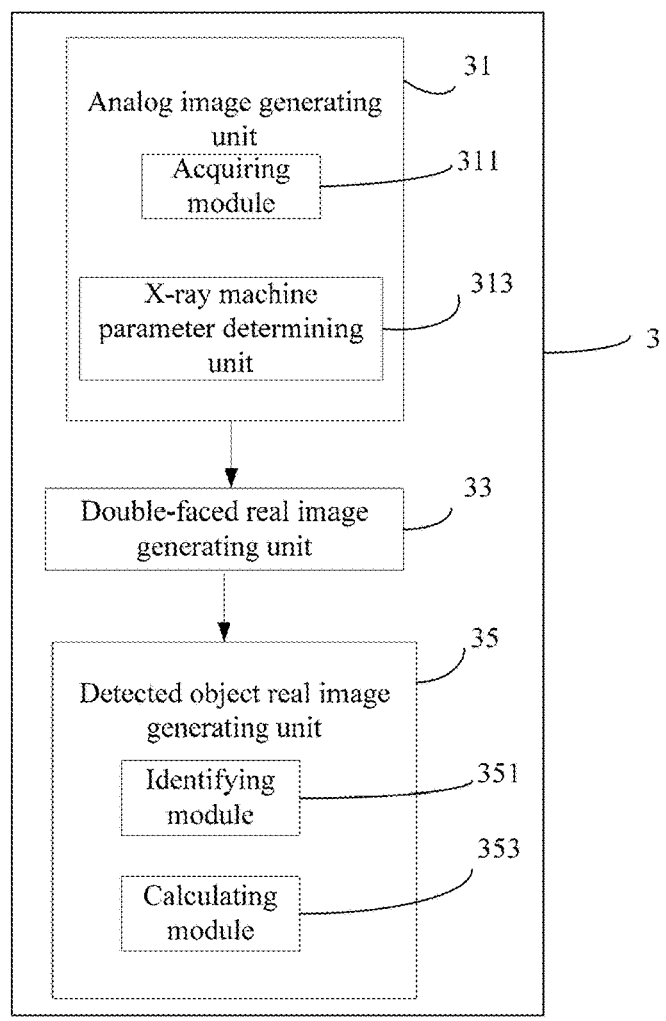
FIG. 3 is a schematic diagram of an apparatus for generating x-ray inspection image of an electronic circuit board according to an embodiment of the present disclosure.

FIG. 3 is a schematic diagram of an apparatus 3 for generating x-ray inspection image of an electronic circuit board according to an embodiment of the present disclosure. As illustrated in FIG. 3, the apparatus 3 includes:

an analog image generating unit 31, configured to respectively generate, according to data files of a electronic circuit board and parameters of an X-ray machine, analog images of both faces of the electronic circuit board.

In some embodiments of the present disclosure, the electronic circuit board may have a double-faced electronic circuit board structure, and the data files of the electronic circuit board may include CAD coordinate data of the electronic circuit board, a line design file of a printed circuit board and a component database; wherein the CAD coordinate data may be exported from the design file of the electronic circuit board; the component parameters may be selected from a component standard library; if some special components are not defined in the standard library, a special component library may be defined by customization of users, and desired special components may be selected therefrom; the parameters of the X-ray machine may include X-ray tube voltage and/or target current; the parameters of the X-ray machine may be predefined or determined according to the line design file and the component parameters.

A double-faced real image generating unit 33, configured to subject the electronic circuit board to X-ray imaging to generate a real image of the electronic circuit board, the real image including real image elements on both faces of the electronic circuit board.

In some embodiments of the present disclosure, the electronic circuit board may be directly subjected to X-ray imaging to generate a double-faced real image covering elements on both front and back faces thereof, wherein the image is the real image of the electronic circuit board, and includes all real elements on the front and back faces of the electronic circuit board.

A detected object real image generating unit 35, configured to identify, according to the analog images of both faces, from the real image an interference image element in the real image that needs to be filtered for generating a real image of the detected object, and filter the interference image element from the real image to generate the real image of the detected object.

In some embodiments of the present disclosure, the process that an interference image element that needs to be filtered from the real image for generating a real image of a detected object is identified from the real image according to the analog images of both faces may include: identifying, according to analog images of both faces, from the real image real image elements corresponding to the analog images of both faces, and determining the interference image element that needs to be filtered from the real image for generating the real image of the detected object; wherein the analog images of both faces may be analog images of either face of the analog images of both faces generated by the analog image generating unit, and in the specific identification process computer software may be employed to compare the analog images with the real image to find the real image elements corresponding to the analog images from the real image. In addition, to generate the real image of the detected object, the interference image elements in the real image need to be filtered, wherein the interference image elements are a part or all of the real image elements corresponding to the analog images, and determination of an interference image element may be based on the analog images and the real image elements of the detected object to be generated.

In some embodiments of the present disclosure, the analog image generating unit 31 includes:

an acquiring module 311, configured to acquire CAD coordinates data of the electronic circuit board, a line design file of a printed circuit board; and acquire component parameters from a component database; and an X-ray machine parameter determining module 313, configured to pre-define or determine the parameters of the X-ray machine according to the line design file and the component parameters.

In the embodiment of the present disclosure, the detected object real image generating unit 35 includes:

an identifying module 351, configured to identify, according to the analog images of both faces, from the real image real image elements corresponding to the analog images of both faces, and determine the interference image element that needs to be filtered from the real image for generating the real image of the detected object.

In some embodiments of the present disclosure, the identifying module 351 may identify, according to a front analog image, from the real image a front real image element corresponding to the front analog image, and determine an interference image element that needs to be filtered from the front real image for generating a back real image; or identify, according to a back analog image, from the real image a back real image element corresponding to the back analog image, and determine an interference image element that needs to be filtered from the back real image for generating a front real image; and a calculating module 353, configured to filter image features of the interference image element using image features of the real image to generate the real image of the detected object.

In some embodiments of the present disclosure, the process that the interference image element is filtered from the real image to generate the real image of the detected object may include: filtering image features of the interference image element using image features of the real image to generate the real image of the detected object. The image features may include imaging gray scale and/or pixel.

In some embodiments of the present disclosure, a person skilled in the art may, in combination with the description in the embodiment, employ other methods to filter the real image elements corresponding to the analog images from the real image to obtain the real image of the detected object, which is not limited in the present disclosure. Any solution of generating the real image of the detected object via identification and calculation attained by a person skilled in the art according to the analog images in the embodiment of the present disclosure shall fall within the protection scope of the present disclosure.

In some embodiments of the present disclosure, the analog images and the real images may be two-dimensional images or may be three-dimensional images or images generated by other means. Any image segmentation solution using the analog image technology according to the embodiment of the present disclosure shall fall within the protection scope of the present disclosure.

Figure 17:
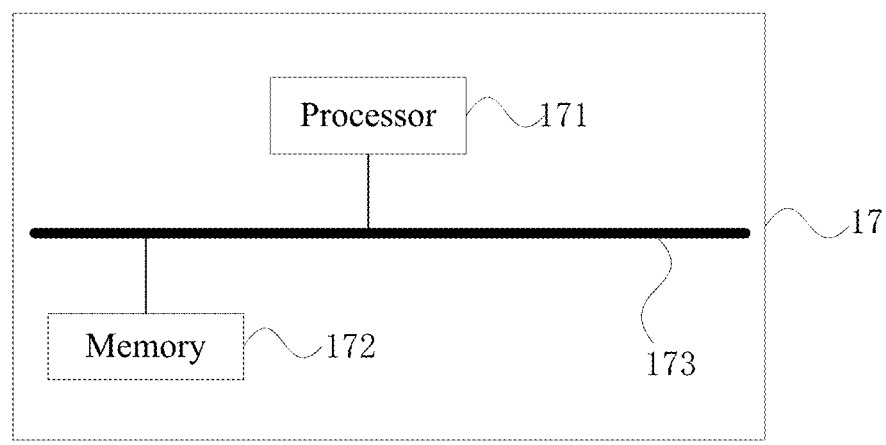
FIG. 17 is a schematic diagram of an apparatus for generating x-ray inspection image of an electronic circuit board according to an embodiment of the present disclosure.

FIG. 17 is a schematic diagram of an apparatus for generating x-ray inspection image of an electronic circuit board according to an embodiment of the present disclosure. In the practice of the present disclosure, as shown in FIG. 17, the apparatus 17 may be an image processing device integrated in a computer, which includes a processor 171, a memory 172 and a bus 173. The processor 171 and the memory 172 are both connected to the bus 173.

The processor 171 is configured to:

respectively generate, according to data files of a electronic circuit board and parameters of an X-ray machine, analog images of both faces of the electronic circuit board;

subject the electronic circuit board to X-ray imaging to generate a real image of the electronic circuit board, the real image including real image elements on both faces of the electronic circuit board; and identify, according to the analog images of both faces, from the real image an interference image element that needs to be filtered from the real image for generating a real image of a detected object, and filter the interference image element from the real image to generate the real image of the detected object.

The above operations performed by the processor 171 may be stored in a memory 172 in the form of a program segment, and when the above operations need to be performed, this program segment is called into the processor 171 to perform the operations.

Figure 4:
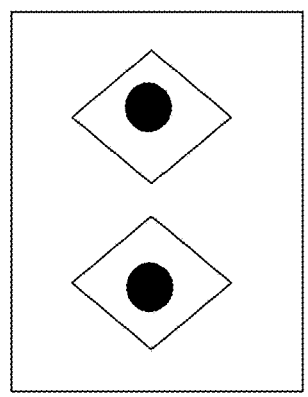
FIG. 4 is a schematic diagram of a double-faced real image of a double-faced electronic circuit board according to an embodiment of the present disclosure.
Figure 5:
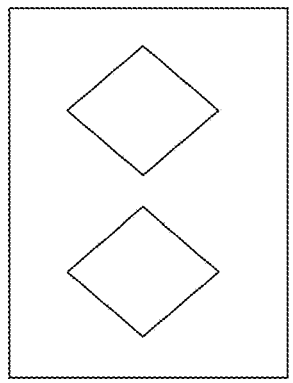
FIG. 5 is a schematic diagram of a front analog image of a double-faced electronic circuit board according to an embodiment of the present disclosure.
Figure 6:
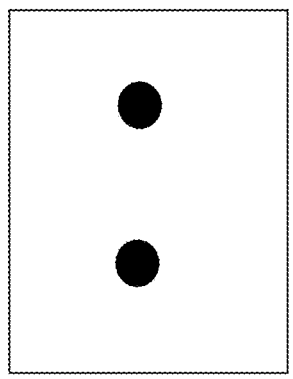
FIG. 6 is a schematic diagram of a back real image of a double-faced electronic circuit board according to an embodiment of the present disclosure.

Some embodiments of the present disclosure are described in detail with reference to FIG. 4, FIG. 5 and FIG. 6. FIG. 4 is a schematic diagram of a double-faced real image of an electronic circuit board. FIG. 5 is a schematic diagram of a front analog image of an electronic circuit board according to an embodiment of the present disclosure. FIG. 6 is a schematic diagram of a back real image of an electronic circuit board according to an embodiment of the present disclosure. FIG. 4 covers front and back images, which, however, cause interference to each other and thus fail to be distinguished. To obtain the real image of the detected object, for example, the back real image, the embodiments of the present disclosure may employ the following steps:

1. inputting data files of the front and back electronic circuit boards into a computer;
2. setting basic X-ray machine parameters;
3. generating front and back analog X-ray images simulated by the computer, for example, the schematic diagram of a front analog X-ray image of the electronic circuit board as illustrated in FIG. 5;
4. subjecting the electronic circuit board to normal X-ray imaging, for example, generating the schematic diagram of a double-faced real image of real image elements on the front and back faces of the electronic circuit board as illustrated in FIG. 4;
5. identifying, by the computer, front image elements from the real X-ray image (for example, as illustrated in FIG. 4) according to the simulated real front image features, for example, gray scale and/or pixel (for example, as illustrated in FIG. 5), and subtracting the feature values (for example, gray scale and/or pixel) of the front image elements from the real image by means of calculation; and
6. obtaining a back real image of the electronic circuit board (for example, as illustrated in FIG. 6).

Through the above steps, the back real image of the electronic circuit board of the detected object is obtained.

Figure 7:
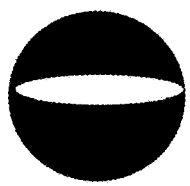
FIG. 7 and FIG. 8 are schematic diagrams of imaging of a double-faced electronic circuit board at different angles of an X-ray machine according to an embodiment of the present disclosure.
Figure 8:
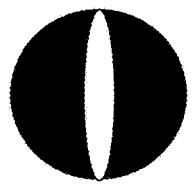

In some embodiments of the present disclosure, the parameters of the X-ray machine may further include: X-ray tube angle or detector angle. To obtain more complete information of the detected object, an image receiver of the X-ray machine or the electronic circuit board or the X-ray tube (which depends on different design structures) may be rotated by a specific angle to carry out X-ray imaging. For example, FIG. 7 and FIG. 8 are schematic diagrams of imaging of a double-faced electronic circuit board at different angles of the X-ray machine. FIG. 7 and FIG. 8 give schematic imaging diagrams before and after a 90-degree rotation of the X-ray machine. Obtaining complete information of the detected object by adjusting the X-ray tube angle or detector angle is very necessary. For example, when the front and back faces of the detected object are the same in shape and size but the detected object has two welding points with different thicknesses, if imaging is carried out for the front and back faces in the perspective of the plain view angle, it may not be identified whether there are two welding points having the same shape and size because in the images of the front and back faces, the image elements with regard to these two welding points. However, if the X-ray machine is adjusted by a specific angle, for example, adjusting the X-ray machine by 90 degrees and then carrying out imaging, the image elements with regard to these welding points in the generated images of the front and back faces are different since these two welding points have different thicknesses.

Figure 9:
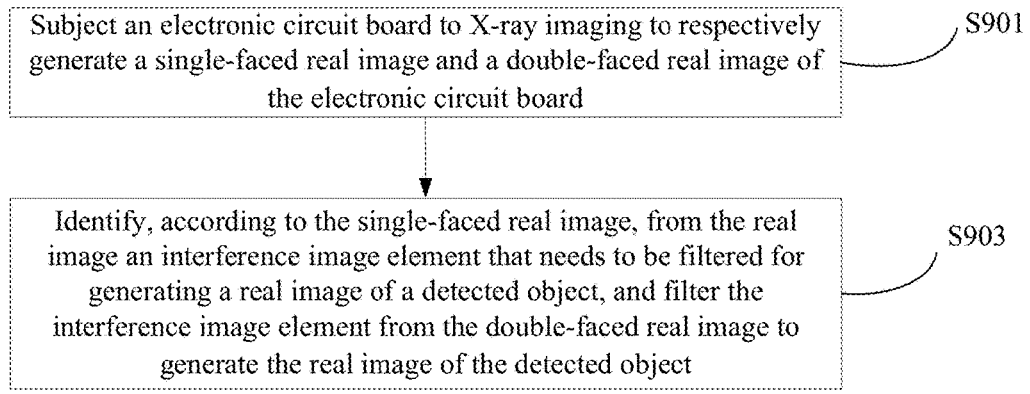
FIG. 9 is a method for generating x-ray inspection image of an electronic circuit board according to another embodiment of the present disclosure.

FIG. 9 is a schematic flowchart of a method for generating x-ray inspection image of an electronic circuit board according to another embodiment of the present disclosure. As illustrated in FIG. 9, the method includes the following steps:

S901: An electronic circuit board is subjected to X-ray imaging to respectively generate a single-faced real image and a double-faced real image of the electronic circuit board.

In some embodiments of the present disclosure, the electronic circuit board may be directly subjected to X-ray imaging to respectively generate a single-faced real image covering elements on one face of the electronic circuit board, and a double-faced real image covering elements on both (front and back) faces of the electronic circuit board. Consistent parameters of the X-ray machine are used in the generating of the single-faced real image and the double-faced real image.

The parameters of the X-ray machine may include: X-ray tube voltage, X-ray tube angle, detector angle, resolution and/or target current.

Generating the real images of a single face of the electronic circuit board may be welding electronic components on a single face of a PCB board and then subjecting the PCB board to X-ray imaging to obtain a single-faced real image of the electronic circuit board; welding electronic components on the other face of the PCB board to obtain a double-faced electronic circuit board, and subjecting the double-faced electronic circuit board to X-ray imaging under the same X-ray machine parameters to obtain a double-faced real image.

In some embodiments of the present disclosure, a printed circuit board for manufacturing the electronic circuit board to may be individually subjected to X-ray imaging to generate a real image of the printed circuit board. The real image of the printed circuit board itself may be used as the detected object, or the interference image element that needs to be filtered for generating the real image of the detected object may be identified from the double-faced real image according to the single-faced real image and the real image of the printed circuit board; and image features of the interference image element may be filtered using image features of the double-faced real image to generate the real image of the detected object.

S903: An interference image element that needs to be filtered for generating a real image of a detected object is identified from the double-faced real image according to the single-faced real image, and the interference image element is filtered from the double-faced real image to generate the real image of the detected object.

In some embodiments of the present disclosure, the process that an interference image element that needs to be filtered for generating a real image of a detected object is identified from the real image according to the single-faced real image may include: identifying, according to the single-faced real image, from the double-faced real image real image elements corresponding to the single-faced real image, and determine the interference image element that needs to be filtered for generating the real image of the detected object; wherein the single-faced image may be the real image of either face generated in step S901, and in the specific identification process computer software may be employed to compare the single-faced real image with the double-faced real image to find the real image elements corresponding to the single-faced real image from the double-faced real image. In addition, to generate the real image of the detected object, the interference image elements in the double-faced real image need to be filtered, wherein the interference image elements are a part or all of the real image elements corresponding to the single-faced real image, and determination of an interference image element may be based on the single-faced real image and the real image of the detected object to be generated.

In some embodiments of the present disclosure, the process that the interference image element is filtered from the double-faced real image to generate the real image of the detected object may include: filtering image features of the interference image element using image features of the double-faced real image to generate the real image of the detected object. The image features may include imaging gray scale and/or pixel.

In some embodiments of the present disclosure, the interference image element that needs to be filtered for generating the real image of the detected object may be identified from the double-faced real image according to the single-faced real image and the real image of the printed circuit board, and the interference image element may be filtered from the double-faced real image to generate the real image of the detected object. The detected object may be a single-faced real image or may be a defined part of component or may be a real image of the printed circuit board.

If the detected object is a single-faced real image, the process that an interference image element that needs to be filtered from the double-faced real image for generating a real image of a detected object is identified from the real image according to the single-faced real image may include:

identifying, according to a front real image and the real image of the printed circuit, from the double-faced real image real image elements corresponding to the front real image, and determining an interference image element that needs to be filtered for generating a back real image; or identifying, according to a back real image and the real image of the printed circuit, from the double-faced real image real image elements corresponding to the back real image, and determining an interference image element that needs to be filtered for generating a front real image.

If the detected object is a defined part of component, the process that an interference image element that needs to be filtered from the double-faced real image for generating a real image of a detected object is identified from the real image according to the single-faced real image may include:

identifying, according to the single-faced real image and the real image of the printed circuit, from the double-faced real image real image elements corresponding to the single-faced real image and the real image of the printed circuit board, and determining an interference image element that needs to be filtered from the double-faced real image for generating a real image of the defined part of component.

If the detected object is a real image of a printed circuit board, the process that an interference image element that needs to be filtered from the double-faced real image for generating a real image of a detected object is identified from the real image according to the single-faced real image and the real image of the printed circuit board may include:

identifying, according to the single-faced real image and the real image of the printed circuit, from the double-faced real image real image elements corresponding to the back real image, and determining an interference image element that needs to be filtered from the double-faced real image for generating the real image of the printed circuit board.

In some embodiments of the present disclosure, a person skilled in the art may, in combination with the description in the embodiment, employ other methods to filter the real image elements corresponding to the real images of both faces from the real image to obtain the real image of the detected object, which is not limited in the present disclosure. Any solution of generating the real image of the detected object via identification and calculation attained by a person skilled in the art according to the single-faced real image in the embodiment of the present disclosure shall fall within the protection scope of the present disclosure.

In some embodiments of the present disclosure, the real images may be two-dimensional images or may be images of other types. Any image filtering solution using the single-faced real image technology according to the embodiment of the present disclosure shall fall within the protection scope of the present disclosure.

According to the embodiment of the present disclosure, by using generated single-faced real images, an interference image element that needs to be filtered is identified from a double-faced real image, and a real image of a detected object is obtained by means of data calculation. In this way, on-line inspection of a double-faced electronic circuit board is implemented. With the method according to the present disclosure, online batchwise inspections do not need the CT technology. In addition, the method addresses the problem of X-ray image interference of the double-faced electronic circuit board, greatly simplifies the online inspection device of the electronic circuit board, and reduces the inspection device cost, and improves the inspection efficiency.

Figure 10:
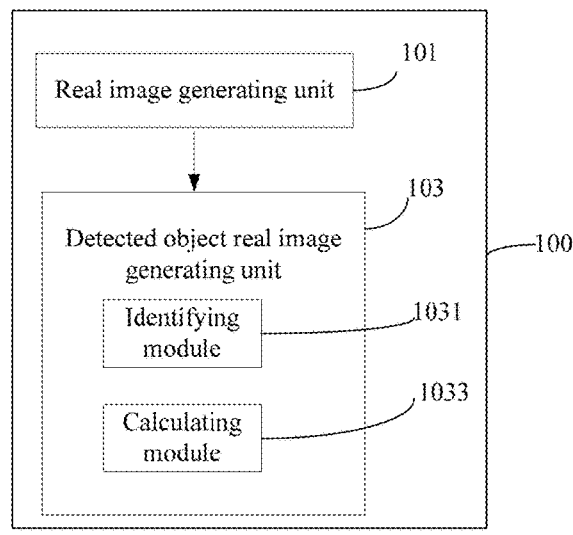
FIG. 10 is a schematic diagram of an apparatus for generating x-ray inspection image of an electronic circuit board according to another embodiment of the present disclosure.

FIG. 10 is a schematic diagram of an apparatus 100 for generating x-ray inspection image of an electronic circuit board according to another embodiment of the present disclosure. As illustrated in FIG. 10, the apparatus 100 includes:

a real image generating unit 101, configured to subject an electronic circuit board to X-ray imaging to respectively generate a single-faced real image and a double-faced real image of the electronic circuit board; and in some embodiments of the present disclosure, the electronic circuit board may be directly subjected to X-ray imaging to respectively generate a single-faced real image covering elements on one face of the electronic circuit board, and a double-faced real image covering elements on both (front and back) faces of the electronic circuit board. Consistent parameters of the X-ray machine are used in the generating of the single-faced real image and the double-faced real image;

the parameters of the X-ray machine may include: X-ray tube voltage, X-ray tube angle, detector angle, resolution and/or target current;

generating the real images of both faces of the electronic circuit board may be welding electronic components on one face of a PCB board and then subjecting the PCB board to X-ray imaging to obtain a single-faced real image of the electronic circuit board; welding electronic components on the other face of the PCB board to obtain a double-faced electronic circuit board, and subjecting the double-faced electronic circuit board to X-ray imaging under the same X-ray machine parameters to obtain a double-faced real image; and a detected object real image generating unit 103, configured to identify, according to the single-faced real image, from the real image an interference image element that needs to be filtered for generating a real image of a detected object, and filter the interference image element from the double-faced real image to generate the real image of the detected object.

In the embodiment of the present disclosure, the detected object real image generating unit 103 includes:

an identifying module 1031, configured to identify, according to the single-faced real image, from the double-faced real image real image elements corresponding to the single-faced real image, and determine the interference image element that needs to be filtered for generating the real image of the detected object.

In some embodiments of the present disclosure, the identifying module 1031 may identify, according to a front real image, from the double-faced real image front real image elements corresponding to the front real image, and determine an interference image element that needs to be filtered for generating a back real image; or identify, according to a back real image, from the double-faced real image back real image elements corresponding to the back real image, and determine an interference image element that needs to be filtered for generating a front real image; and a calculating module 1033, configured to filter image features of the interference image element using image features of the double-faced real image to generate the real image of the detected object.

In some embodiments of the present disclosure, the process that the interference image element is filtered from the double-faced real image to generate the real image of the detected object may include: filtering image features of the interference image element using image features of the double-faced real image to generate the real image of the detected object. The image features may include imaging gray scale and/or pixel.

In some embodiments of the present disclosure, a person skilled in the art may, in combination with the description in the embodiment, employ other methods to filter the real image elements corresponding to the single-faced real image from the double-faced real image to obtain the real image of the detected object, which is not limited in the present disclosure. Any solution of generating the real image of the detected object via identification and calculation attained by a person skilled in the art according to the single-faced real image in the embodiment of the present disclosure shall fall within the protection scope of the present disclosure.

In some embodiments of the present disclosure, the real images may be two-dimensional images or may be three-dimensional images or images generated by other means. Any image segmentation solution using the single-faced real image technology according to the embodiment of the present disclosure shall fall within the protection scope of the present disclosure.

In some embodiments, the processor 171 can also be configured to:

subject an electronic circuit board to X-ray imaging to respectively generate a single-faced real image and a double-faced real image of the electronic circuit board; and identify, according to the single-faced real image, from the double-faced real image an interference image element that needs to be filtered for generating a real image of a detected object, and filter the interference image element from the double-faced real image to generate the real image of the detected object.

The above operations performed by the processor 171 may be stored in a memory 172 in the form of a program segment, and when the above operations need to be performed, this program segment is called into the processor 171 to perform the operations.

Figure 11:
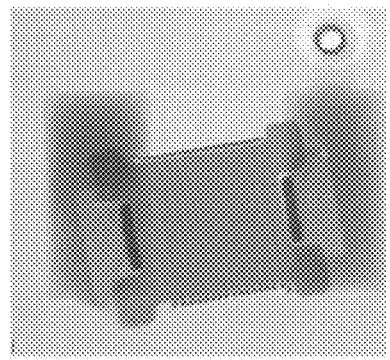
FIG. 11 is a schematic diagram of a front real image of a double-faced electronic circuit board according to another embodiment of the present disclosure.
Figure 12:
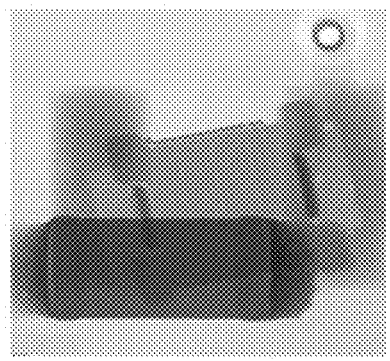
FIG. 12 is a schematic diagram of a double-faced real image of a double-faced electronic circuit board according to another embodiment of the present disclosure.
Figure 13:
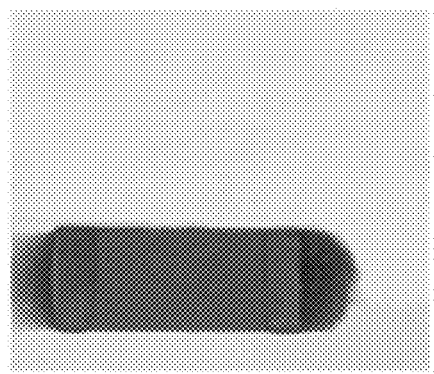
FIG. 13 is a schematic diagram of a back real image calculated and separated from a double-faced electronic circuit board according to another embodiment of the present disclosure.

Some embodiments of the present disclosure are described in detail with reference to FIG. 11, FIG. 12 and FIG. 13. FIG. 11 is a schematic diagram of a front real image of a double-faced electronic circuit board according to an embodiment of the present disclosure. FIG. 12 is a schematic diagram of a double-faced real image of a double-faced electronic circuit board according to an embodiment of the present disclosure. FIG. 3 is a schematic diagram of a back real image calculated and separated from a double-faced electronic circuit board according to another embodiment of the present disclosure. FIG. 12 covers front and back images, which, however, cause interference to each other and thus fail to be distinguished. To obtain the real image of the detected object, for example, the back real image, the embodiments of the present disclosure may employ the following steps:

1. subjecting an electronic circuit including component on the front face to X-ray imaging to generate a real image of the front electronic circuit board;

2. ensuring that consistent parameters of the X-ray machine in generating the front real image are used, and subjecting the electronic circuit board including electronic components on both faces thereof to X-ray imaging;

3. identifying, by a computer, front image elements from the double-faced real X-ray image according to the real front image features, for example, gray scale and/or pixel, and subtracting the feature values (for example, gray scale and/or pixel) of the front image elements from the double-faced real image by means of calculation; and 4. obtaining a back real image of the electronic circuit board (for example, as illustrated in FIG. 13).

Through the above steps, the back real image of the electronic circuit board of the detected object is obtained.

Figures 14, 15:
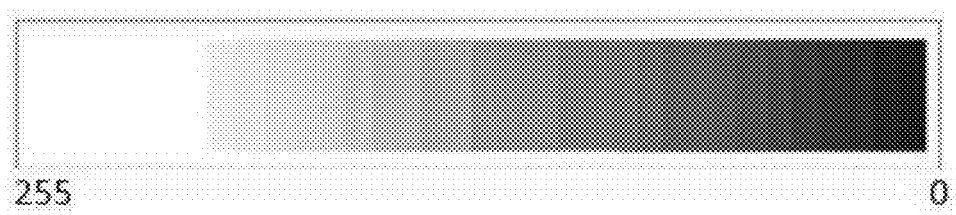
FIG. 14 is a schematic diagram of block sampling of a 256-order gray scale according to an embodiment of the present disclosure.
FIG. 15 is a schematic diagram of straight stripe gradual changes of a 256-order gray scale according to an embodiment of the present disclosure.
Figure 16:
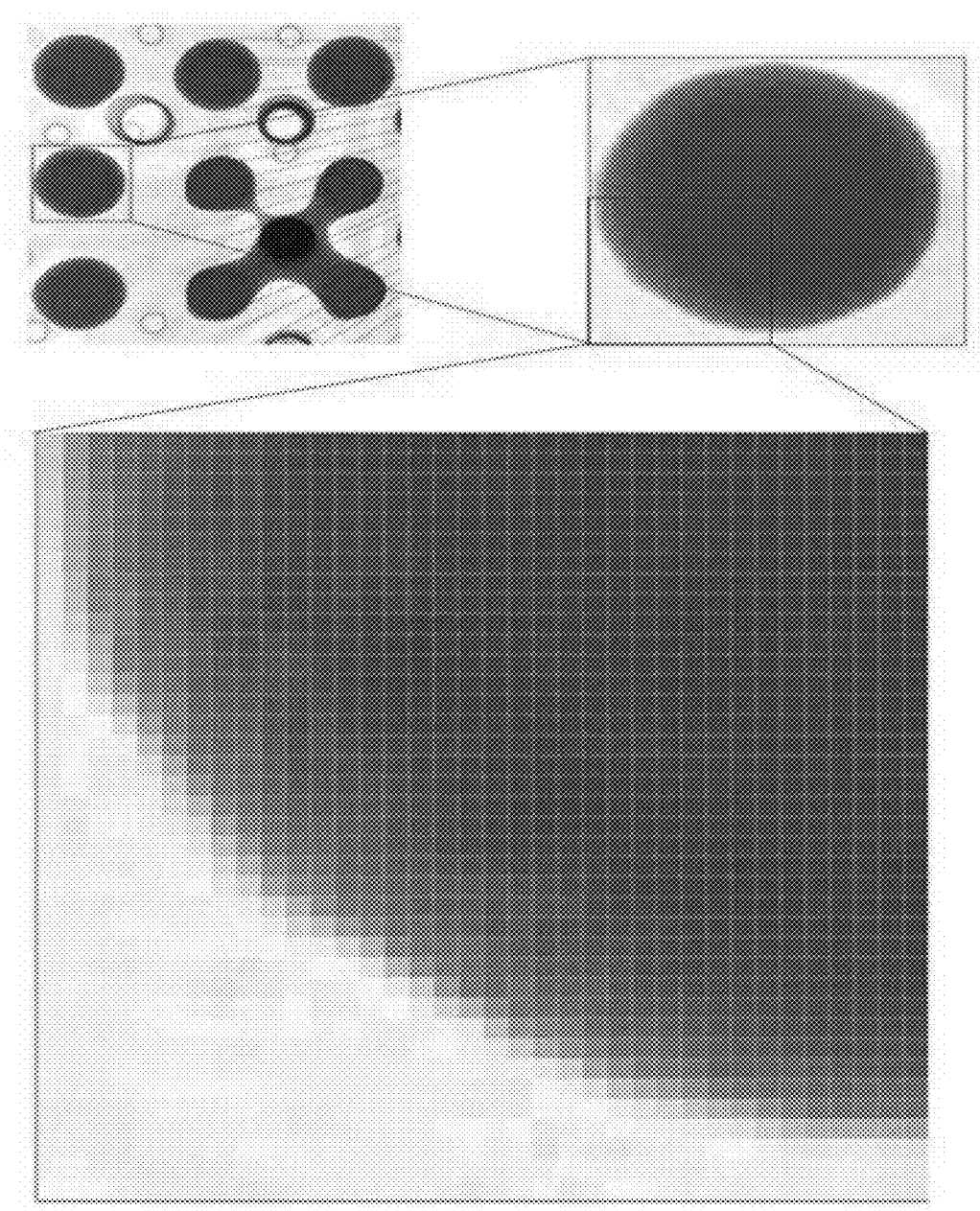
FIG. 16 is a schematic diagram of image pixel decomposition using an X-ray machine according to an embodiment of the present disclosure.

Obtaining a real image of a detected object by means of image calculation using gray scale is further illustrated with reference to FIG. 14, FIG. 15 and FIG. 16. FIG. 14 is a schematic diagram of block sampling of a 256-order gray scale according to an embodiment of the present disclosure. FIG. 15 is a schematic diagram of straight stripe gradual changes of a 256-order gray scale according to an embodiment of the present disclosure. FIG. 16 is a schematic diagram of image pixel decomposition using an X-ray machine according to an embodiment of the present disclosure.

In some embodiments of the present disclosure, for example, the image presented by the X-ray machine is a picture displayed based on the black-and-white luminance value. The black-and-white luminance may be divided into several grades of values. The black-and-white luminance values obtained via such division are gray scales, and the commonly used is 256-order gray scale division. An X-ray image is formed of thousands of pixels, and the grid of each pixel is filled with a gray scale. The finally displayed is the X-ray image that is commonly seen. As illustrated in FIG. 16, each grid is filled with a number representing a gray scale. When it is ensured that the X-ray penetrates through a multi-layer sample, a multi-layer image obtained by the X-ray machine may be considered an image presented after the numbers representing the gray scales in all the pixel grids of all the layers.

Using a double-layer circuit board as an example, if the image of one layer and images of the two layers are already known, by using the principle of gray scale imaging, the image of the other layer may be separated via calculation. As such, the problem of mutual interference between the multiple layers during X-ray inspection, such that convenient and rapid inspection is achieved.

In the embodiments of the present disclosure, the analog images and the real images may be two-dimensional images or may be three-dimensional images or images of other types. Any image segmentation solution using the analog image or single-faced image technology according to the embodiments of the present disclosure shall fall within the protection scope of the present disclosure.

According to the embodiments of the present disclosure, by using generated analog images, an interference image element that needs to be filtered is identified from a real image, and a real image of a detected object is obtained by means of data calculation. In this way, on-line inspection of a double-faced electronic circuit board is implemented. With the method according to the present disclosure, online batchwise inspections do not need the CT technology. In addition, the method addresses the problem of X-ray image interference of the double-faced electronic circuit board, greatly simplifies the online inspection device of the electronic circuit board, and reduces the inspection device cost, and improves the inspection efficiency. As such, the method and apparatus according to the present disclosure may be applied to online inspections of electronic circuit boards.

It should be noted that the specification and drawings of the present disclosure illustrate exemplary embodiments of the present disclosure. However, the present disclosure may be implemented in different manners, and is not limited to the embodiments described in the specification. The embodiments described are not intended to limit the present disclosure, but are directed to rendering a thorough and comprehensive understanding of the disclosure of the present disclosure. In addition, the above described technical feature may incorporate and combine with each other to derive various embodiments not illustrated in the above specification, and such derived embodiments shall all be deemed as falling within the scope of the disclosure contained in the specification of the present disclosure. Further, a person skilled in the art may make improvements or variations according to the above description, and such improvements or variations shall all fall within the protection scope as defined by the claims of the present disclosure.

What is claimed is:

1. A method for generating x-ray inspection image of an electronic circuit board, the method comprising:
   respectively generating, according to data files of the electronic circuit board and parameters of an X-ray machine, analog images of both faces of the electronic circuit board;
   subjecting the electronic circuit board to X-ray imaging to generate a real image of the electronic circuit board, the real image comprising real image elements on both faces of the electronic circuit board;
   identifying, according to the analog images of both faces, from the real image an interference image element that needs to be filtered from the real image for generating a real image of a detected object; and
   filtering the interference image element from the real image to generate the real image of the detected object.

2. The method according to claim 1, wherein
   the data files of the electronic circuit board comprise: CAD coordinates data of the electronic circuit board, a line design file of a printed circuit board and a component database;
   a standard component library is generated from the component database according to component package-related standards, and special components are generated by customization; and
   the parameters of the X-ray machine comprise: X-ray tube voltage, X-ray tube angle, detector angle and/or target power.

3. The method according to claim 2, wherein the respectively generating, according to data files of a electronic circuit board and parameters of an X-ray machine, analog images of both faces of the electronic circuit board comprises:
   acquiring the CAD coordinates data of the electronic circuit board and the line design file of the printed circuit board from the data files of the electronic circuit board;
   acquiring component parameters from the component database; and
   respectively generating the analog images of both faces of the electronic circuit board according to the CAD coordinates data of the electronic circuit board, the line design file of the printed circuit board, the component parameters and the parameters of the X-ray machine, and with reference to imaging rules of different X-ray devices under different parameters of the X-ray machines.

4. The method according to claim 3, wherein the parameters of the X-ray machine are predefined or determined according to the line design file and the component parameters.

5. The method according to claim 1, wherein the identifying, according to the analog images of both faces, from the real image an interference image element that needs to be filtered from the real image for generating a real image of a detected object, and filtering the interference image element from the real image to generate the real image of the detected object comprises:
   identifying, according to the analog images of both faces, from the real image real image elements corresponding to the analog images of both faces;
   determining the interference image element that needs to be filtered from the real image for generating the real image of the detected object; and
   filtering image features of the interference image element using image features of the real image to generate the real image of the detected object.

6. The method according to claim 5, wherein the identifying, according to the analog images of both faces, from the real image real image elements corresponding to the analog images of both face, and determining the interference image element that needs to be filtered from the real image for generating the real image of the detected object comprises:
   identifying, according to a front analog image, from the real image a front real image element corresponding to the front analog image; and
   determining an interference image element that needs to be filtered from the front real image for generating a back real image; or identifying, according to a back analog image, from the real image a back real image element corresponding to the back analog image; and determining an interference image element that needs to be filtered from the back real image for generating a front real image.

7. The method according to claim 6, wherein the image features comprise imaging gray scale and/or pixel.

8. The method according to claim 1, wherein the analog image and the real image comprise a two-dimensional image.

9. A method for generating x-ray inspection image of an electronic circuit board, comprising:

subjecting the electronic circuit board to X-ray imaging to respectively generate a single-faced real image and a double-faced real image of the electronic circuit board;

identifying, according to the single-faced real image, from the double-faced real image an interference image element that needs to be filtered for generating a real image of a detected object; and filtering the interference image element from the double-faced real image to generate the real image of the detected object.

10. The method according to claim 9, wherein consistent parameters of the X-ray machine are used in the generating of the single-faced real image and the double-faced real image.

11. The method according to claim 10, wherein the parameters of the X-ray machine comprise: X-ray tube voltage, X-ray tube angle, detector angle, resolution and/or target current.

12. The method according to claim 9, wherein the identifying, according to the single-faced real image, from the real image an interference image element that needs to be filtered for generating a real image of a detected object, and filtering the interference image element from the double-faced real image to generate the real image of the detected object comprises:

identifying, according to the single-faced real image, from the double-faced real image real image elements corresponding to the single-faced real image;

determining the interference image element that needs to be filtered for generating the real image of the detected object; and filtering image features of the interference image element using image features of the double-faced real image to generate the real image of the detected object.

13. The method according to claim 12, wherein the identifying, according to the single-faced real image, from the double-faced real image real image elements corresponding to the single-faced real image, and determining the interference image element that needs to be filtered for generating the real image of the detected object comprises:

identifying, according to a front real image, from the double-faced real image real image elements corresponding to the front real image; and determining an interference image element that needs to be filtered for generating a back real image; or identifying, according to a back real image, from the double-faced real image real image elements corresponding to the back real image; and determining an interference image element that needs to be filtered for generating a front real image.

14. The method according to claim 9, further comprising: independently subjecting a printed circuit board for manufacturing the electronic circuit board to X-ray imaging to generate a real image of the printed circuit board; and the identifying, according to the single-faced real image, from the real image an interference image element that needs to be filtered for generating a real image of a detected object, and filtering the interference image element from the double-faced real image to generate the real image of the detected object comprises:

identifying, according to the single-faced real image and the real image of the printed circuit board, from the double-faced real image the interference image element that needs to be filtered for generating the real image of the detected object; and filtering image features of the interference image element using image features of the double-faced real image to generate the real image of the detected object.

15. The method according to claim 9, wherein the identifying, according to the single-faced real image and the real image of the printed circuit board, from the double-faced real image the interference image element that needs to be filtered for generating the real image of the detected object comprises:

identifying, according to the front real image and the real image of the printed circuit board, from the double-faced real image the interference image element that needs to be filtered for generating the back real image; or identifying, according to the back real image and the real image of the printed circuit board, from the double-faced real image the interference image element that needs to be filtered for generating the front real image; or identifying, according to the front real image, the back real image and the real image of the printed circuit board, from the double-faced real image the interference image element that needs to be filtered for generating the real image of the printed circuit board.

16. The method according to 12, wherein the image features comprise imaging gray scale and/or pixel.

17. The method according to claim 9, wherein the real image comprises a two-dimensional image.

18. An apparatus for generating x-ray inspection image of an electronic circuit board, comprising:

at least one processor; and a memory communicably connected with the at least one processor for storing instructions executable by the at least one processor, wherein execution of the instructions by the at least one processor causes the at least one processor to:

respectively generate, according to data files of the electronic circuit board and parameters of an X-ray machine, analog images of both faces of the electronic circuit board;

subject the electronic circuit board to X-ray imaging to generate a real image of the electronic circuit board, the real image comprising real image elements on both faces of the electronic circuit board; and identify, according to the analog images of both faces, from the real image an interference image element in the real image that needs to be filtered for generating a real image of the detected object, and filter the interference image element from the real image to generate the real image of the detected object.

19. An apparatus for generating x-ray inspection image of an electronic circuit board, comprising:

at least one processor; and a memory communicably connected with the at least one processor for storing instructions executable by the at least one processor, wherein execution of the instructions by the at least one processor causes the at least one processor to:

subject an electronic circuit board to X-ray imaging to respectively generate a single-faced real image and a double-faced real image of the electronic circuit board; and identify, according to the single-faced real image, from the double-faced real image an interference image element that needs to be filtered for generating a real image of a detected object, and filter the interference image element from the double-faced real image to generate the real image of the detected object.

20. A non-transitory computer-readable storage medium storing executable instructions, wherein when executed by an apparatus, causes the apparatus to:

respectively generate, according to data files of a electronic circuit board and parameters of an X-ray machine, analog images of both faces of the electronic circuit board;

subject the electronic circuit board to X-ray imaging to generate a real image of the electronic circuit board, the real image comprising real image elements on both faces of the electronic circuit board; and identify, according to the analog images of both faces, from the real image an interference image element in the real image that needs to be filtered for generating a real image of the detected object, and filter the interference image element from the real image to generate the real image of the detected object.

21. A non-transitory computer-readable storage medium storing executable instructions, wherein when executed by an apparatus, causes the apparatus to:

subject an electronic circuit board to X-ray imaging to respectively generate a single-faced real image and a double-faced real image of the electronic circuit board; and identify, according to the single-faced real image, from the double-faced real image an interference image element that needs to be filtered for generating a real image of a detected object, and filter the interference image element from the double-faced real image to generate the real image of the detected object.

* * * * *